(12) United States Patent
DesJardins et al.

(10) Patent No.: US 8,858,979 B1
(45) Date of Patent: Oct. 14, 2014

(54) SERVICE INDUCED BYPRODUCTS FOR LOCALIZED DRUG DELIVERY IN ORTHOPAEDIC IMPLANTS

(75) Inventors: John D. DesJardins, Clemson, SC (US); Martine LaBerge, Seneca, SC (US); Cassandra Wright-Walker, Pickens, SC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 13/360,020

(22) Filed: Jan. 27, 2012

Related U.S. Application Data (60) Provisional application No. 61/437,258, filed on Jan. 28, 2011.

(51) Int. Cl.
  *A61L 27/14* (2006.01)
(52) U.S. Cl.
  USPC ........................ 424/423; 427/2.27; 623/16.11
(58) Field of Classification Search
  USPC ........................................ 623/23.72; 424/423
  See application file for complete search history.

(56) References Cited

U.S. PATENT DOCUMENTS

| | | | |
|---|---|---|---|
| 5,338,731 A | 8/1994 | Breuer et al. | |
| 5,646,134 A | 7/1997 | Yates | |
| 5,827,904 A | 10/1998 | Hahn | |
| 5,876,446 A | 3/1999 | Agrawal et al. | |
| 6,448,315 B1 | 9/2002 | Lidgren et al. | |
| 6,692,758 B1 | 2/2004 | Ito et al. | |
| 7,074,432 B2 | 7/2006 | Dasch et al. | |
| 7,651,701 B2 | 1/2010 | Meyer et al. | |
| 2006/0003917 A1 | 1/2006 | Aspenberg et al. | |
| 2009/0319044 A1* | 12/2009 | Lee ............................ | 623/16.11 |

FOREIGN PATENT DOCUMENTS

WO  WO 2004/105824 A1  9/2004

OTHER PUBLICATIONS

Al-Saffar N, et al. (1994) Role of newly formed vessels and cell adhesion molecules in the tissue response to wear products from orthopaedic implants. Journal of Materials Science: Materials in Medicine 5: 813-818.
Attar FG, et al. (2008) Survivorship analysis at 15 years of cemented press-fit condylar total knee arthroplasty. The Journal of Arthroplasty 23: 344-349.
Bastian P, et al. (2005) Local delivery of bisphosphonate from coated orthopedic implants increases implants mechanical stability in osteoporotic rats. Journal of Biomedical Materials Research 76A: 133-43.
Bartel DL, et al. (1986) The effect of conformity, thickness, and material on stresses in ultra-high molecular weight components for total joint replacement. The Journal Of Bone And Joint Surgery. American vol. 68: 1041-1051.
Bartl R, et al. (2007) Bisphosphonates in medical practice, 1st ed. New York: Springer; 265 p.
Benson LC, et al. (2001) Effects of in vitro wear of machined and molded UHMWPE tibial inserts on TKR kinematics. Journal of Biomedical Materials Research 58: 496-504.
Chowdhury SKR, et al. (2004) Wear characteristic and biocompatibility of some polymer composite acetabular cups. Wear 256: 1026-1036.
Cornelio RB et al. (2009) "Quantification of Sodium Alendronate by LC Anion Exchange Using in Line Complexation", J Liq Chromatogr Related Technol. 32:2857-2865.
Crossett L. (2006) Evolution of the low contact stress (LCS) complete knee system. Orthopedics 29: S17-S22.
Duffy GP, et al. (2007) Hybrid total knee arthroplasty analysis of component failures at an average of 15 years. The Journal of arthroplasty 22: 1112-1115.
Galetz MC, et al. (2007) Carbon nanofibre-reinforced ultrahigh molecular weight polyethylene for tribological applications. Journal of Applied Polymer Science 104: 4173-4181.
Iwase M, et al. (2002) A novel bisphosphonate inhibits inflammatory bone resorption in a rat osteolysis model with continuous infusion of polyethylene particles. Journal of Orthopaedic Research 20: 499-505.
Jalali-Vahid D, et al. (2001) Prediction of lubricating film thickness in a ball-in-socket model with a soft lining representing human natural and artificial hip joints. Proceedings of the Institution of Mechanical Engineers—Part J—Journal of Engineering Tribology 215: 363-372. (Abstract Only).
Jasty MJ, et al. (1986) Localized osteolysis in stable, non-septic total hip replacement. The Journal of Bone and Joint Surgery. American vol. 68: 912-919.
Kurtz SM, et al. (1999) Advances in the processing, sterilization, and cross linking of ultra-high molecular weight polyethylene for total joint arthroplasty. Biomaterials 20: 1659-1688.
Lane JM, et al. (2001) Bisphosphonate therapy in fibrous dysplasia. Clinical orthopaedics and related research 6-12. (Abstract Only).
Lehmann HJ, et al. (2002) Effect of bisphosphonates on cartilage turnover assessed with a newly developed assay for collagen type II degradation products. Annals of the Rheumatic Diseases 61: 530-533.

(Continued)

*Primary Examiner* — Gina C Justice
(74) *Attorney, Agent, or Firm* — Dority & Manning, P.A.

(57) ABSTRACT

A composite material including ultra-high molecular weight polyethylene in conjunction with a biologically active agent is described. The biologically active agent can be, for example, an anti-osteolytic agent such as a bisphosphonate. The composite material can be utilized in forming implants such as total joint replacement implants. The biologically active agent can be released from the composite material either from the bulk or from wear particles released from the surface of the implant component during use. Upon release, the biologically active agent can carry out the intended function of the agent.

19 Claims, 7 Drawing Sheets

(56) References Cited

OTHER PUBLICATIONS

McKellop H et al. (1981) Friction and wear properties of polymer, metal, V and ceramic prosthetic joint materials evaluated on a multichannel screening device. Journal of Biomedical Materials Research 15: 619-653. (Abstract Only).

Oral E, et al. (2006) Migration stability of alpha-tocopherol in V irradiated UHMWPE. Biomaterials 27: 2434-2439.

Oral E, et al. (2006) The effect of alpha-tocopherol on the oxidation and free radical decay in irradiated UHMWPE. Biomaterials 27:5580-5587.

Oral E, et al. (2006) Wear resistance and mechanical properties of highly cross-linked, ultrahigh-molecular weight polyethylene doped with vitamin E. The Journal of Arthroplasty 21: 580-591.

Parasnis NC, et al. (1998) Analysis of the effect of pressure on compression moulding of UHMWPE. J Mater Sci-Mater Med 1998; 9:165-172.

Ralston SH, et al., (1989) Clinical, biochemical, and radiographic effects of aminohydroxypropylidene bisphosphonate treatment in rheumatoid arthritis. Annals of the Rheumatic Diseases 48: 396-399.

Rand JA, et al. (2003) Factors affecting the durability of primary total knee prostheses. The Journal Of Bone And Joint Surgery. American vol. 85A: 259-265.

Reno F, et al. (2004) The induction of MMP-9 release from granulocytes by vitamin E in UHMWPE. Biomaterials 25: 995.

Reno F, et al. (2006) UHMWPE and vitamin E bioactivity: An emerging perspective. Biomaterials 27: 3039-3043.

Rogers MJ (2003) New insights into the molecular mechanisms of action of bisphosphonates. Current pharmaceutical design 9: 2643-2658.

Schmalrized TP, et al. (1992) Periprosthetic bone loss in total hip arthroplasty. Polyethylene wear debris and the concept of the effective joint space. The Journal Of Bone And Joint Surgery. American vol. 74: 849-863.

Sabokbar A, Rushton N. (1995) Role of inflammatory mediators and adhesion molecules in the pathogenesis of aseptic loosening in total hip arthroplasties. The Journal of Arthroplasty 10: 810-816.

Shanbhag AS et al. (1997) The John Charnley Award. Inhibition of wear debris mediated osteolysis in a canine total hip arthroplasty model. Clinical orthopaedics and related research 33-43. (Abstract Only).

Shibata N, et al. (2003) Defect initiation at subsurface grain boundary as a precursor of delamination in ultrahigh molecular weight polyethylene. Journal of Biomedical Materials Research. Part A 67: 276-284.

Vessely MB, et al. (2006) The Chitranjan Ranawat award: Long-term survivorship and failure modes of 1000 cemented condylar total knee arthroplasties. Clinical orthopaedics and related research 452: 28-34. (Abstract Only).

Willert HG, et al. (1990) Osteolysis in alloarthroplasty of the hip. The role of ultra-high molecular weight polyethylene wear particles. Clinical orthopaedics and related research 95-107 (Abstract Only).

Wright TM, et al. (1988) Analysis of surface damage in retrieved carbon fiber-reinforced and plain polyethylene tibial components from posterior stabilized total knee replacements. Journal of Bone and Joint Surgery—American vol. 70A: 1312-1319.

Xu JW, et al. (1998) Interleukin-11 (IL-11) in aseptic loosening of total hip replacement (THR). Scandinavian Journal Of Rheumatology 27: 363-367. (Abstract Only).

\* cited by examiner

SERVICE INDUCED BYPRODUCTS FOR LOCALIZED DRUG DELIVERY IN ORTHOPAEDIC IMPLANTS

CROSS REFERENCE TO RELATED APPLICATION

The present application claims filing benefit of U.S. Provisional Patent Application Ser. No. 61/437,258 having a filing date of Jan. 28, 2011 entitled "UHMWPE and Its Service Induced Byproducts as Localized Drug Delivery Carriers For Use In Orthopaedic Bearing Applications," which is incorporated herein in its entirety.

BACKGROUND OF THE INVENTION

Each year in the United States there is an increasing trend of patients receiving total joint replacement (TJR) procedures. As reported by the National Center for Health Statistics in 2004, total hip replacements (THRs) have risen to 234,000 per year and total knee replacements (TKRs) have risen to 478,000. This is in part due to revision surgeries, but also due to patients receiving TKRs at younger ages because of higher consumer demand and improved surgical outcomes. Additionally, surgeons have begun allowing patients in their 80s and later, even with co-morbid conditions, to receive TKR implants in order to increase quality of life, thus also increasing the total number of implant procedures.

Unfortunately, joint longevity is an increasing problem, particularly in light of the younger ages of patients. As the age of patients' receiving arthroplasty decreases, there is increasing interest in longevity of the implant life to reduce the number of potential revisions a patient must undergo. Failure rates vary drastically due to, e.g., design; cemented, hybrid, or non-cemented implant; and age at implantation. Similarly, failure can be caused by a variety of factors including, e.g., infection, stress shielding, pen-prosthetic osteonecrosis or fracture, implant instability, polyethylene wear-through or fracture, allergy or hypersensitivity. The most common cause of failure of an implant is implant loosening resultant of wear and osteolysis.

The use of ultra high molecular weight polyethylene (UHMWPE) inserts in total knee replacements, though relatively inert, result in wear particle-caused osteolysis, the predominant cause for prosthesis failure and revision surgery. The release of polymer particles due to wear of the implant surface leads to macrophage activation which subsequently activates osteoclasts via cytokine release. Osteoclasts cause bone resorption and loosening of the implant, and the cycle continues until failure. Even with the highest performing polymer found to date for joint replacement, ultra-high molecular weight polyethylene (UHMWPE), particle formation has been found to exist irrelevant of the counterpart bearing surface.

In an attempt to alleviate this problem, bisphosphonates have been utilized via oral systemic delivery. While bisphosphonates can decrease periprosthetic osteolysis, this method requires the patient to periodically ingest the agents for the life of the implant. Potential problems with such delivery routes include the need for the patient to remember to take the medication as well as the need for the patient to have long-term access to the medication. In addition, the systemic delivery and the high solubility of bisphosphonates result in a predominant portion being excreted via the kidney without reaching its target as well as the possibility of unintended consequences due to the circulation of the bisphosphonates throughout the patient's system.

What are needed in the art are UHMWPE composite materials that can alleviate problems found in joint replacements, for instance problems associated with the release of particles from the materials due to wear. What are also needed are composite materials that can take advantage of the existence of wear particles formed during use of the implant.

SUMMARY OF THE INVENTION

Disclosed in one embodiment is a composite that includes UHMWPE and a biologically active agent. For example, the biologically active agent can be present in the composite in an amount of up to about 5% by weight of the composite.

Also disclosed is a joint replacement that includes a component comprising the UHMWPE composite, the UHMWPE composite including a biologically active agent.

Methods of forming a joint replacement are also disclosed. For example, a method can include combining an UHMWPE with a biologically active agent to form a composite and then shaping the composite to form a component of the joint replacement such that the component comprises a wear surface.

BRIEF DESCRIPTION OF THE FIGURES

The present disclosure may be better understood with reference to the following figures:

FIG. 3 illustrates tensile testing results on UHMWPE composites, testing results include Modulus of Elasticity [MPa] (FIG. 3A), Yield Stress at 0.3% Strain [MPa] (FIG. 3B), Ultimate Load [N] (FIG. 3C), Ultimate Stress at Failure [MPa] (FIG. 3D), and Toughness [MPa] (FIG. 3E).

FIG. 6 illustrates the results of a 28-day elution test of ALN from 15 μm thin film slices of an UHMWPE composite as described herein (FIG. 6A) including an expansion plot of first 24 hours (FIG. 6B).

FIG. 7 illustrates the results of 28-day elution test of ALN from bulk UHMWPE composite blocks (FIG. 7A) including an expansion plot of the first 48 hours of release (FIG. 7B).

DETAILED DESCRIPTION

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment may be used in another embodiment to yield a still further embodiment. Thus, it is intended that the present invention cover such modifications and variations as come within the scope of the appended claims and their equivalents.

The present disclosure is generally directed to an UHMWPE composite that can be utilized in joint replacements. More specifically, the UHMWPE composite includes a biologically active agent. For example, in one embodiment the biologically active agent can reduce or prevent osteolysis in and near the joint, i.e., an anti-osteolytic biologically active agent. Through utilization of the composite UHMWPE in a joint replacement, the inherent wear of the UHMWPE can be utilized as a drug delivery approach over a long-term delivery period. Moreover, in those embodiments in which an anti-osteolytic agent is incorporated in the composite, the inherent wear characteristics of the UHMWPE can be less problematic, as the anti-osteolytic biologically active agent of the composite can be released during the course of the joint lifetime and prevent or reduce periprosthetic osteolysis due to the implant.

The biologically active agent can beneficially be released from the bulk composite material and/or from wear particles formed from the bulk composite material in the joint area. Beneficially, the increased surface area of a particle formed due to wear at the surface of an UHMWPE component can encourage release of the biologically active agent from the composite following formation of the wear particle. For instance, upon formation of the wear particle, the biologically active agent incorporated in the particle can more quickly be released into the surrounding area as compared to the release rate of the agent while still in the bulk composite material of the joint. Following release of the agent, the biologically active agent can provide a beneficial service in or near the joint replacement area. For instance, when considering an anti-osteolytic and/or osteogenic agent such as a bisphosphonate, following release of the bisphosphonates from either the bulk component or a micro-sized wear particle, the bisphosphonates can bind to remodeling bone thereby slowing resorption of the bone while upregulating the presence of osteoblasts to increase new bone formation.

The biologically active agents can be delivered to the joint lubricant, joint tissues and/or other areas of the joint that are either directly or indirectly exposed to the UHMWPE material due to, e.g., service induced/mechanically induced expulsion, material biodegradation, diffusion, or by direct contact of the bearing material or its wear induced by-products to the biological media in question. Beneficially, through utilization of a bulk UHMWPE composite bearing, biologically active agents can be directly delivered to sites within the joint and surrounding tissues via the bulk material and/or the wear particles that are produced during implant service with little or none of the biologically active agent systemically circulated.

The release of a biologically active agent directly into the joint capsule either by the UHMWPE bulk or by the wear debris that is generated as a result of bearing service can provide many benefits to a joint replacement system. First, a localized delivery of biologically active agent(s) into the joint capsule can decrease the need for minimally invasive injections and/or oral delivery of the biologically active agent to the joint capsule. Second, the local delivery dosage could be substantially less than what would be needed if the biologically active agent were systemically administered. Third, the localized agent delivery could be tailored to occur in a time release fashion by regulating leaching/degradation/wear rates from the bulk. Fourth, when wear induced particles of the UHMWPE composite are produced; the agent can be carried by these particles into the joint. Fifth, material in the form of wear particles would be exposed to accelerated delivery potential from increased surface area to bulk volume ratios. Sixth, with the migration of the wear particle into the joint fluid and surrounding tissues, the wear particles can act as localized delivery carriers to transport the biologically active agent into areas other than where the bulk UHMWPE composite exists. Seventh, the process of wear is continuous and occurs at a steady rate throughout the service lifetime of the bearing implant. As such, the delivery of biologically active agents over time can serve as a service-lifetime delivery method in joint replacements. Eighth, the inclusion of anti-osteolytic drugs can be tailored into a per-wear particle dose to combat osteolysis one wear particle at a time. Ninth, the migration of wear particles and/or migration of agents released from the composite could aide in the delivery of a wide variety of types of biologically active agents, bioactive marker and/or radioactive agent to areas in which the wear particles are known to migrate, both locally and systemically. Tenth, the specific distribution or concentrated placement of an agent into the UHMWPE component (e.g., near the surface, sub-surface, layered, columnar, edge specific, etc.) can allow for concentrated or varied time/wear release of biologically active agent based upon the wear rates of the material.

The UHMWPE composite can include any type or grade of UHMWPE that is suitable for use in an implantable component. Generally, the UHMWPE can have a weight average molecular weight of between about $2 \times 10^6$ and about $6 \times 10^6$, as is known, and a high impact strength combined with a low coefficient of friction, making this the best polymer found to date for use in joint replacements.

Implant grade UHMWPE is available from a variety of commercial sources including, without limitation, Ticona of Florence, Ky.; Braskem of Sao Paulo, Brazil; and Mitsui, of Japan. In one embodiment, GUR® UHMWPE resin available from Ticona can be utilized in forming the composite.

In addition to the UHMWPE, the composite includes one or more biologically active agents. In one embodiment, the biologically active agent can function as an anti-osteolytic biologically active agent that can directly or indirectly prevent osteolysis.

In one embodiment, the UHMWPE composite can include one or more bisphosphonates as the biologically active agent. Bisphosphonates (also called diphosphonates) belong to a class of drugs that can not only inhibit bone resorption and as such can function as an anti-osteolytic agent, but can also encourage the development of new bone growth and function as an osteogenic agent. Specifically, bisphosphonates have been shown to reduce osteoclastic activity and can prevent UHMWPE wear debris induced osteolysis following arthroplasty upon release from the composite.

Bisphosphonates are synthetic compounds that contain a P—C—P backbone and are structurally similar to naturally occurring pyrophosphate. As the name diphosphonates suggests, the backbone contains two phosphonate groups ($PO_3$) covalently bonded to a carbon atom. The carbon atom is also bound to the two side chains that define the chemical properties (potency, pharmokinetics, etc) of the specific bisphosphonates compound. Bisphosphonates encompassed herein include those having the chemical structure:

wherein R1 and R2 are independent of one another and may be hydrogen; hydroxyl; halogen; substituted or non-substituted alkyl, aryl, or heterocyclic; nitrogenous or non-nitrogenous; and the like.

In one embodiment, one of the side chains is a hydroxide (—OH) group, which can improve solubility of the bisphosphonate. Table 1, below, presents the R1 and R2 side chains for several different FDA approved bisphosphonates encompassed herein. Of course, bisphosphonates as may be included in a composite are in no way intended to be limited to the exemplary materials described in Table 1.

TABLE 1

| Agent | R1 | R2 |
|---|---|---|
| Alendronate | —OH | —(CH$_2$)$_3$—NH$_2$ |
| Etidronate | —OH | —CH$_3$ |
| Ibandronate | —OH | —CH$_2$—CH$_2$—N(CH$_3$)(CH$_2$)$_4$CH$_3$ |
| Pamidronate | —OH | —CH$_2$—CH$_2$—NH$_2$ |
| Risedronate | —OH | —CH$_2$-(3-pyridyl) |
| Tiludronate | —H | —S—(4-chlorophenyl) |
| Zoledronate | —OH | —CH$_2$-(imidazolyl) |
| Clodronate | —Cl | —Cl |
| Neridronate | —OH | —(CH$_2$)$_5$—NH$_2$ |
| Olpadronate | —OH | —(CH$_2$)$_2$N(CH$_3$)$_2$ |

The biologically active agent incorporated in the UHMWPE composite is not limited to bisphosphonates. Any biologically active agent that can be released from the composite, either from the bulk or from wear particles formed during use of the composite, and can be of benefit in and/or around the area of the implant can be incorporated in the composite. For instance, and without limitation, biologically active agents can include one or more of anti-osteolytic agents in addition to or alternative to bisphosphonates such as osteoprotegerin (OPG) or TNF-α inhibitors (e.g. Etanercept); osteogenic agents (growth factors (e.g. TGF-β and BMP-2), FORTEO® (teriparatide [rDNA origin] injection), calcitonin (Miacalcin), gallium-containing compounds (e.g. Ganite)), chondrogenic, chondral inductive, chondral conductive, and/or osteoconductive agents (e.g., growth factors such as bone-derived growth factors, calcium phosphates or other ceramic materials, calcium sulfate, bioactive glasses and glass-ceramics, demineralized bone matrix, etc.), analgesics (e.g., acetaminophen, ibuprofen, butorphanol, narcotic analgesics), anticoagulants (e.g., heparin, hirudin and hirudin analogs such as hirulog), immunosuppressives, anti-inflammatories (e.g., non-steroidal anti-inflammatory agents), antibiotics, oncology treatments, antiviral agents, polynucleotide agents (e.g., siRNA, RNAi, nucleoside anticancer drugs, vaccines), small molecule agents (e.g., alkaloids, glycosides, phenols), anti-infection agents (e.g., interferons, interleukins), muscle contractives inhibitors and/or relaxants (prostaglandin antagonists, prostoglandins), Anti-fungal (e.g., imidazoles, polyenes), and so forth.

Combinations of biologically active agents can be utilized. For instance, patients suffering from osteoporosis or other bone degenerating conditions may benefit from having implants comprising osteogenic inductive materials in conjunction with the biologically active agent that prevents osteolysis.

In general, the UHMWPE composite can include the biologically active agent in an amount such that presence of the agent does not significantly affect the material characteristics of the composite as compared to a composite that does not include the biologically active agent. For instance, the composite can include the biologically active agent in an amount of up to about 5% by weight of the composite. In one embodiment, the UHMWPE composite can include the biologically active agent in an amount of between about 1% and about 4% by weight of the composite, for example the composite can include the biologically active agent in an amount of about 2% by weight of the composite. The preferred amount of the biologically active agent included in the composite can depend upon the wear rate of the UHMWPE material as well as the desired dosage of the agent at the implant site. For example, when considering a total knee replacement joint, it has been estimated about 20 mm$^3$ UHMWPE particles are released per million cycles (approximately 1 year) of implantation life and that there are approximately 1 billion wear particles generated per year. A calculated average particle diameter (from wear debris volume and approximate numbers) is about 3.4 microns. Using this coupled with reported data for the biologically active agent, a targeted concentration can be calculated. For instance, when considering the bisphosphonates alendronate, it has been estimated that a concentration of about $10^{-4}$M can inhibit cell proliferation and there exists an increase in cell proliferation when concentration is between $10^{-7}$ and $10^{-8}$M. Thus, given the wear particle concentration and size estimates, a loading level of about 2% by weight of the UHMWPE composite can be targeted.

The inclusion of a biologically active agent will generally not affect material characteristics of the UHMWPE composite as compared to a similar UHMWPE component that does not include any agent. In one embodiment, however, the inclusion of the biologically active agent can lead to a drop in elastic modulus of the composite as compared to an UHMWPE component that does not include the biologically active agent. This may be mechanically advantageous in forming a component for a replacement joint, as the component may yield improved lubrication when utilized in vivo. For example, the UHMWPE composite can exhibit a modulus of elasticity that is between about 2% and about 10% less than, or about 5% less than an UHMWPE that is of similar composition, but for the inclusion of the biologically active agent.

In addition to one or more biologically active agents, the UHMWPE composite can include additives as are generally known in the art such as, without limitation, reinforcement additives such as fibrous fillers, processing additives, plasticizers, impact modifiers, colorants, stabilizers, lubricants, additional biologically active additives, biomarking agents, and so forth. Of course, in those embodiments in which the UHMWPE composites are for use in vivo, any additives should be acceptable for such application. Wider variation of additives may be possible for other applications, for example in in vitro testing applications.

Fibrous additives can include fibers of any suitable size and material. For example, carbon fibers, para-aramid fibers (e.g., Kevlar® fibers), and the like can be incorporated in the composites.

In one embodiment, the composite can be self-reinforced UHMWPE composite, also referred to as an UHMWPE homocomposite. In this embodiment the composite can include UHMWPE in fiber or fabric form along with the UHMWPE matrix. By way of example, the composite can include Spectra fibers, UHMWPE solution spun fibers, including Spectra 900, Spectra 1000, and Spectra 2000 fibers.

In another embodiment, the UHMWPE composite can include one or more biomarkers, for instance a radioactive agent. Such additives can be utilized to track degradation of the implant as well as track migration of wear particles following release of the particles from the surface of the implant.

The UHMWPE and the biologically active agent can be combined according to any suitable formation process to form the composite. For example, UHMWPE in powder, granular, or chip form can be melt processed with the biologically active additive to form a composite material that can be further processed to the desired shape. For example, the UHMWPE composite can be melt extruded and then machined into its final form or direct molded using, e.g., compression molding.

A component formed of the UHMWPE composite can include the biologically active agent either homogeneously or heterogeneously throughout the component. For instance, in one embodiment a component can include the agent in a predetermined heterogeneous pattern throughout the component so as to improve and/or control release of the agent from the component during use.

The component formed of the UHMWPE composite can include one or more wear surfaces. A wear surface can be those surfaces of the component that can contact another component of a joint replacement or a bone surface following implant and during use of the joint. Thus, a wear surface will be those surfaces of a component from which wear particles can be released during use. In one embodiment, the concentration of the biologically active agent can be greater at the wear surface(s) of the component than deeper within the component. For instance, greater than about 70% by weight of the biologically active agent can be distributed from the wear surface to a depth of about 2 mm of the wear surface of the formed component.

In another embodiment, a component can include one or more layers of high concentration biologically active agent sandwiched between areas of low concentration. For example, a larger concentration of one or more biologically active agents can be held in a layer that is generally parallel to the wear surface of the formed component, but at a depth beneath the surface as originally formed. According to this embodiment, a larger concentration of the biologically active agent can be released following a period of initial wear of the component. In another embodiment, a larger concentration of the biologically active agent can be located throughout the depth of the UHMWPE composite component, but in a generally columnar distribution that correlates at the wear surface with the geometry of the contacting surface of the mating component.

A component formed of the UHMWPE composite that includes the biologically active agent in a heterogenous distribution can be formed according to any suitable process. By way of example, in one embodiment a melt formation process can be utilized in which the melt is extruded with periodic additions of the biologically active agent to the melt. Thus, following an addition of the agent to the melt, the melt will extrude at a high concentration of agent. Following, a period of extrusion of the UHMWPE including little or no biologically active agent can be carried out, and so on to form an extrudate with alternating high and low concentration areas of the biologically active agent within the composite. The extrudate can then be shaped as desired such that the high concentration areas of the extrudate are at the desired location (e.g., the outer edge) of the formed component.

In another embodiment, multiple compositions having varied concentrations of one or more biologically active agents can be co-extruded such that adjacent areas of the extrudate can vary in agent concentration. Co-extrusion process can provide the varied concentration materials in any desired geometric configuration include, e.g., parallel layers, core/shell geometries (in which a shell can completely or only partially encircle a core), islands-in-the-sea geometries, and so forth.

The UHMWPE composite can be sterilized according to any suitable methods. For example, in one embodiment the UHMWPE composite can be sterilized according to a gamma sterilization process in an inert (low oxygen) environment. In one embodiment high doses (100 Mrad) of the gamma radiation can be utilized during sterilization in order to increase cross-linking, which has been shown to increase wear resistance while decreasing the occurrence of pitting and delamination in the implanted component. Other sterilization techniques can include, without limitation, ethylene oxide sterilization, gas plasma sterilization, and the like.

The UHMWPE composite can be utilized in one embodiment as a component in a joint replacement implant including a partial joint replacement or a total joint replacement. Joints replacements can be any synovial joint replacement including gliding joints, hinge joints, condyloid joints, saddle joints, ball and socket joints, and compound joints. For example, the UHMWPE can be utilized in a knee replacement, a hip replacement, an elbow replacement, and so on.

Figure 1:
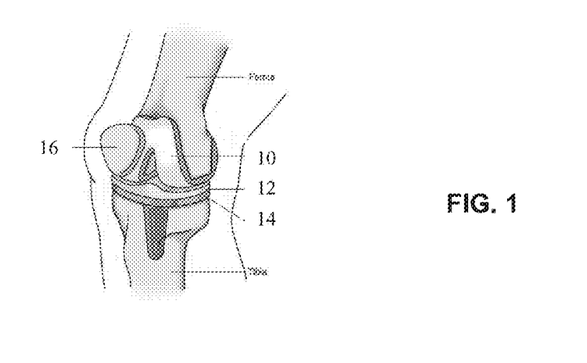
FIG. 1 is a schematic illustrating a typical knee replacement joint as may incorporate the UHMWPE composite as described herein.

In one embodiment, the UHMWPE composite can be utilized to form one or more components of a total knee replacement as is illustrated in FIG. 1. With reference to FIG. 1 a total knee replacement can include a femoral component 10, tibial component 14, tibial insert 12, and patellar button 16.

The femoral and tibial components 10,14 can be formed of any acceptable orthopaedic bearing material such as a cobalt/chromium/molybdenum alloy (CoCrMo), ceramic alloys (alumina or zirconia), or other acceptable orthopaedic materials. The femoral and tibial components 10, 14 are generally either press-fit or cemented over the associated bone (femur or tibia) once it has been surgically prepared. CoCrMo can be utilized in one embodiment for these components as the chromium can add wear resistance and can allow for a passivating oxidation layer of chromium oxide to form on the surface. Further, the cast CoCrMo (see, e.g., ASTM F75) can allow fabrication of a porous surface for bone ingrowth, which is necessary in non-cemented components. The tibial insert 12 can serve as a sacrificial bearing surface for the joint and can be formed of the UHMWPE composite.

The patellar button 16 is an optional component of a total knee joint replacement. The patellar button 16 can also be formed of the UHMWPE composite. In one embodiment, the patellar button can be metal-backed, with the metal surface placed against the surgically refinished patella.

The biologically active agent of the UHMWPE composite can be released from the bulk material and/or from wear particles degraded from the contact surface of the joint component formed of the UHMWPE composite. Following release, the biologically active agent can serve to the desired function, for instance to prevent osteolysis due to the presence of the implant and/or the wear particles from the implant. For example, when considering a bisphosphonate agent, the released bisphosphonate can bind to local bone. For instance, the agent can bind to the exposed hydroxyapatite (HA) sites where bone has already been resorbed.

The first step in prevention of osteolysis by bisphosphonates is "ingestion." By this process, osteoclasts take in the drug along with the HA to which it is bound. After ingestion, non-nitrogenous and nitrogenous bisphosphonates have been shown to use different mechanisms to inhibit bone resorption. Non-nitrogenous bisphosphonates are broken down within the osteoclast yielding a chemical compound that interferes with the cell's adenosine triphosphate (ATP) pathway causing the cell to commence apoptosis, since ATP is necessary as an energy source for osteoclast function. As increased particles of bisphosphonate are bound to bone, osteoclast apoptosis leads to a decrease in the overall number of osteoclasts present and therefore a decrease in the amount of bone that can be resorbed. With a decrease in bone resorption and assuming normal osteoblast function, more bone will then be laid down with respect to that being resorbed thus increasing the overall amount of bone with time.

Nitrogenous bisphosphonates act through the metabolic HMG-CoA reductase pathway. The bisphosphonates disrupt the pathway as they are used in place of the normal pathway chemical, pyridoxal-phosphate (PPi). The disturbance is understood to occur because both compounds contain phosphate groups, and PPi's functions within the pathway as a phosphate group donor. This disruption of the pathway results in minimal rho protein expression. This lack of rho protein detrimentally affects the osteoclast's cytoskeleton such that the osteoclast will lose its 'ruffled border.' Rho protein controls the attachment of the cell membrane to the cytoskeleton, and a lack in its expression leads to a non-nitrogenous bisphosphonates result in the same outcome, osteoclast apoptosis, simply via different mechanisms and pathways.

The disclosure may be better understood with reference to the Examples, set forth below.

Example 1

Studies were conducted to assess the mechanical properties of UHMWPE composite including tensile testing and pin-on-disk tribological testing.

Blocks of UHMWPE composite were prepared using 2% (by weight) dopant of 8-Anilino-1-naphthalenesulfonic acid hemimagnesium salt hydrate (available from Sigma) containing a naphthalene fluorescent tag, blended with UHMWPE powder (GUR® 4150 Ticona). The dopant is hydrophilic and of similar size (MW=310) to alendronate sodium (MW=325.12), which is sold under the brand name Fosamax™ (Merck Inc.).

UHMWPE and the additive were blended using dry mixing via a vortexer (VWR Standard Mini Vortexer; speed=10) for 10 minutes. Additive distribution was determined by visual inspection of the green particles (tag) within the translucent polyethylene matrix.

Following mixing, all UHMWPE specimens were compression molded using a Carver press. Table 2 details the times and pressures used in the compression molding process. For initial tensile testing, a custom mold was used with a molding area of 4580 mm$^2$ (4.4 g polyethylene powder/mm thickness). For all pin-on-disk specimens, a larger custom mold was used containing a molding area of 7960 mm$^2$ (7.4 g polyethylene/mm thickness). For this mold, approximately 187 g of polyethylene was used to achieve a 25.4 mm thick block from which pins were machined.

TABLE 2

| Step | Time (min) | Stage Duration (min) | Force (MPa) | Temperature (° C.) Top | Bottom | Rate deg/min |
|---|---|---|---|---|---|---|
| 1 | 0 | | 38.9 | 29 | 29 | — |
| 2 | 5 | 5 | 7.8 | 29 | 29 | 0 |
| 3 | 20 | 15 | 7.8 | 177 | 215 | 9.9 |
| 4 | 30 | 10 | 7.8 | 177 | 215 | 0 |
| 5 | 57 | 27 | 38.9 | 93 | 140 | −3.1 |
| 6 | 87 | 30 | 38.9 | 93 | 140 | 0 |
| 7 | 107 | 20 | 0 | 29 | 29 | −3.2 |

A uniaxial tensile test was performed on the compression molded samples. Two millimeter thick blocks were prepared and compression molded. Dogbone-shaped specimens (20 mm gage length & 4.9 mm width) were cut from each block using a die following ASTM standard 5937-96. Tensile testing was carried out according to ASTM standard 5937. After specimens were cut, all specimens were cleaned according to ASTM F1715 protocol followed by ethylene oxide sterilization. A total of 86 specimens were used for the tensile test (n=43 for UHMWPE and n=43 for UHMWPE composite).

Specimens were tested to failure at room temperature in air at a constant strain rate of 5 mm/sec using a servohydraulic testing system with a 25 kN load cell (Instron 8874, Instron Corporation, Canton, Mass.). Stress-strain curves were plotted using the results of the tensile test; from these curves several material properties were determined including elastic modulus, yield stress, ultimate stress, and toughness. Yield stress was calculated at 0.3% strain. A Student t-test was used to assess the statistical differences between the material properties of both groups ($\alpha$=0.05).

Results showed that the yield stress of the composite material was not significantly different from that of the control UHMWPE (Table 3). Other material properties were however significantly different including elastic modulus (p=0.004), ultimate stress (p=0.002), and toughness (p<0.001).

TABLE 3

| | | UHMWPE Control | Composite | p-values |
|---|---|---|---|---|
| Elastic Modulus | MPa | 529 ± 38* | 509 ± 37* | 0.004 |
| Yield Stress | MPa | 20 ± 0.7 | 20 ± 0.8 | 0.091 |
| Ultimate Stress | MPa | 38 ± 2.0* | 36 ± 2.0* | 0.002 |
| Max Load | N | 391 ± 21* | 375 ± 20* | 0.002 |
| Ultimate Strain | % | 403 ± 67* | 347 ± 47* | <0.001 |
| Toughness | MPa | 125 ± 24* | 105 ± 18* | <0.001 |

*denotes significance (p < 0.05)

Figure 2:
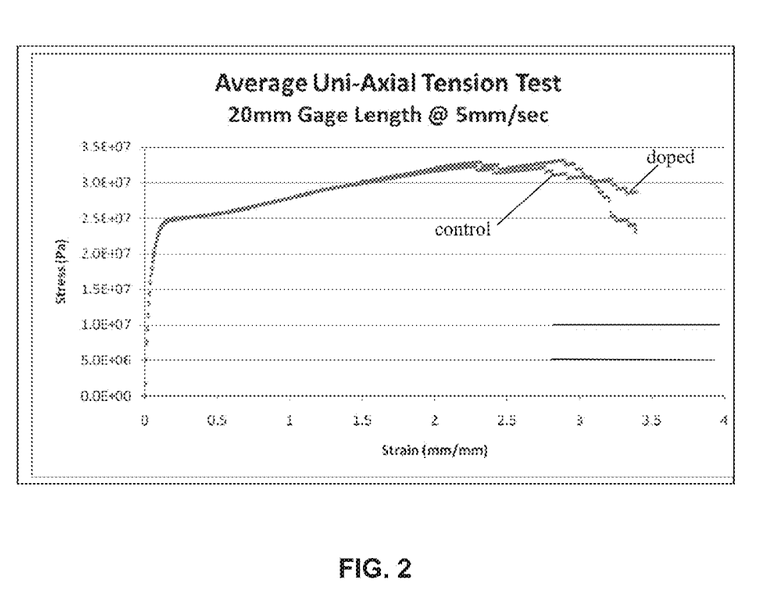
FIG. 2 illustrates stress vs. strain data determined for an UHMWPE composite as described herein.
Figure 3A:
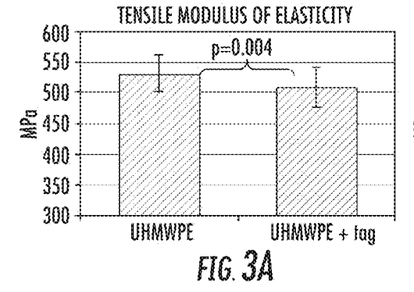
Figure 3B:
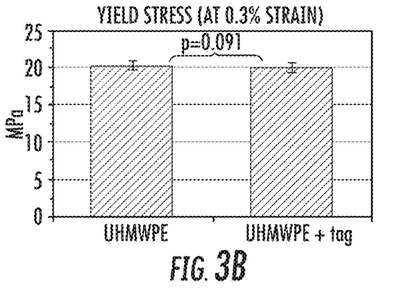
Figure 3C:
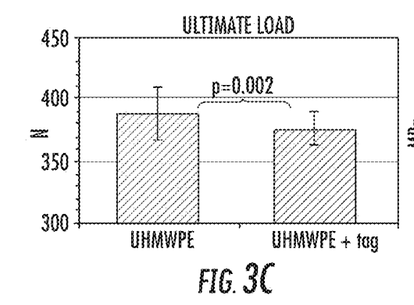
Figure 3D:
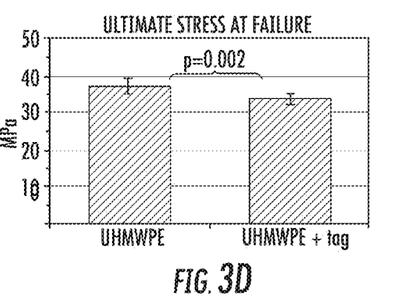
Figure 3E:
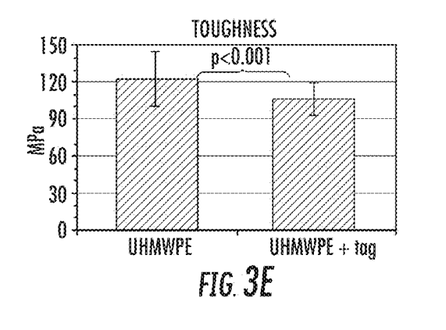

Additional tensile testing results are shown in FIG. 2, which illustrates the stress vs. strain curve and FIG. 3, which illustrates Modulus of Elasticity [MPa] (FIG. 3A), Yield Stress at 3% Strain [MPa] (FIG. 3B), Ultimate Load [N] (FIG. 3C), Ultimate Stress at Failure [MPa] (FIG. 3D), and Toughness [MPa] (FIG. 3E).

Each tribosystem was lubricated with 50 mL of 50% bovine serum (Hyclone) diluted with deionized water+2% w/v sodium azide (NaN$_3$, Sigma) as an anti-microbial agent per station. Samples were tested over a 40 km sliding distance along an elliptical path (110 mm/cycle) with a sliding speed of 50 mm/sec according to ASTM method F732. Pin-on-disk wear tests were conducted with an OrthoPod pin-on-disk tester (AMTI; Watertown, Mass.). Blocks of polyethylene were molded using compression molding as previously described in the larger custom mold. Half inch thick blocks of both UHMWPE and UHMWPE composite were fabricated and pins (9.5 mm diameter with 3 mm flat tip and 20 mm cylindrical section atop the conical tip (n=12)) were cut from each block of polyethylene. This allowed for larger loads to be placed on the pins during pin-on-disk trials, which would allow for sufficient wear to be generated in order to compare the materials. Each tribosystem was lubricated with 25 mL of 50% bovine serum (Hyclone) diluted with deionized water+ 2% w/v sodium azide (NaN$_3$, Sigma) as an anti-microbial agent per station. Samples were tested over a 40 km sliding distance along a circular path (60 mm/cycle) according to ASTM method F732. Loaded soak control specimens under similar conditions to the experimental pins (loaded at approximately 6 MPa pin tip pressure) were used; the portion of the pin that was in fluid was controlled to be similar to that in the OrthoPod due to the hydrophilic nature of the tag.

Diamond-coated CoCrMo specimens ($R_a$=22.4±1.8 nm) were used as the countersurface. These were mounted in custom OrthoPod fixtures. A circle-shaped wear pattern (19 mm Ø) was utilized; a speed of 1 Hz was selected. Data from the experiment was recorded every ½ km over the 40 km. Every 10 km, the machine was disassembled, cleaned, dried, weighed (Mettler Toledo, d=0.01 mg), then reassembled with application of new bovine serum. A two-tailed t-test ($\alpha$=0.05) was used to analyze the results for significance.

Figure 4:
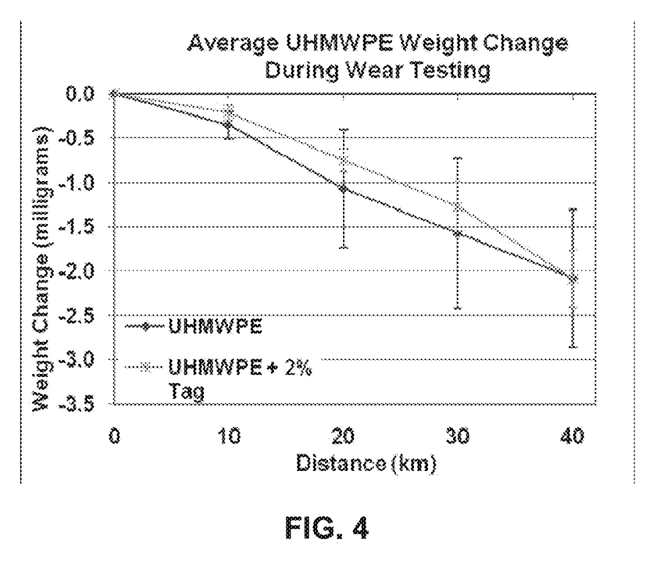
FIG. 4 compares the change in gravimetric weight over 40 km during a pin-on-disk wear test of an UHMWPE composite as described herein and an UHMWPE control.

A preliminary trial using 3 MPa of pressure (n=3 for each UHMWPE and UHMWPE composite) at pin tip using a circle wear pattern did not generate sufficient wear over the 40 km. The force was increased to 42.4N to generate a clinically relevant pin tip pressure of 6 MPa. Two experiments were completed. The 6 MPa pressure did generate sufficient wear over the 40 km trial as illustrated in FIG. 4. However, there was no significant difference in the gravimetric weight loss between the two material types at 40 km (p=0.78).

Example 2

Drug elution tests were performed using small blocks (1.0 cm×1.0 cm×1.0 cm) of polyethylene (n=6) and PE-BP (2% w/w of bisphosphonate, n=6) molded using a custom mold. Each polyethylene specimen was molded using 950±0.5 mg GUR® 4150 UHMWPE. Each PE-BP specimen was molded using the same amount of polyethylene (950±0.5 mg GUR® 4150 UHMWPE) with the addition of 19.4±0.2 mg alendronate sodium, a bisphosphonate (BP). All specimens were compression molded as previously described. Dimensions of each specimen as well as gravimetric weights were obtained prior to the experiment as some material was lost in the compression molding process due to flashing. Data allowed for estimations of actual alendronate content in each block for drug elution calculations. Specimens were not washed prior to drug elution tests to ensure that alendronate would be in a measurable range. Measurements and weights allowed for estimations of actual alendronate content in each block and therefore thin films from each block for drug elution calculations.

In vitro alendronate release study was performed in an environmental chamber maintained at 35°±2° C.; for the duration of the experiment, the specimens undergo shaking using a VWR mini shaker at 300 rpm.

Thin film drug elution tests were performed using thin films (15 µm×1.0 cm×1.0 cm) of UHMWPE and PE-BP (2% w/w) cut (PolycutE, Leica) from 1 cm$^3$ blocks molded using the same mold as bulk elution drug elution tests. Thin films for pilot studies were cut from either the top or the center of blocks of polyethylene and PE-BP. For the experimental studies, 1 slice (0-15 mm) was cut from the outside of 15 separate blocks and placed in a centrifuge tube. A second slice (15-30 mm) was cut from the outside of the 15 blocks and placed in a second centrifuge tube. This pattern was repeated for a total of 8 sample tubes (0-120 um surface depth) of PE-BP (20 'slices': t=15 µm each).

The thin film samples were maintained in 10 mL of HPLC-grade water (Fisher) on a shaker at 37° C. Aliquots of 1 mL was collected at the indicated time intervals (1, 2, 3, 5, and 7 days for the pilot study) with equal amounts of HPLC-grade water being re-added. For the experimental study, aliquots of 1 mL were taken over the course of 28 days with equal amounts of water re-added for (time points in hours): 1, 2, 4, 8, 12, 24, 48 (2 days), 72 (3 days), 120 (5 days), 168 (7 days), 336 (14 days), 404 (21 days), 572 (28 days) with equal fluid amounts being re-added for experimental studies. Samples (n=4; triplicate) were analyzed using high pressure liquid chromatography (HPLC, Waters, Milford, Mass.).

In-line complexation of copper II nitrate with the bisphosphonate and detection via the UV detector was used for detection. A Waters HPLC (Milford, Mass.) with an anion-exchange column (Waters IC-Pak anion HR column) packed with polymethacrylate resin with a quaternary ammonium functional group (6 µm particles size, 4.6×75 mm ID) was used. Parameters included column temperature of 25° C., 0.85 mL/minute flow rate, and injection volume of 50 µL. Dilute nitric acid (Fluka) at a concentration of 6 mM with copper II nitrate (0.5 mM, Alfa Aesar) was used for the mobile phase. A calibration curve was generated prior to beginning any elution experiments. The same HPLC column was used throughout the duration of the elution experiments; further, the column was equilibrated via injection of the standard alendronate solution till reproducible retention times & peak shapes are generated. A 0.4 mg/mL standard alendronate solution was produced by dispersing 2 mg of alendronate sodium in 5 mL of deionized water and stirring for 30 minutes. Then, the solution is passed through a 0.2 µm filter (Nalgene) for HPLC use. Each individual sample was filtered using 0.45 µm polypropylene syringe filters (National Scientific) prior to injection in an HPLC vial (Waters). It was found that the alendronate peak had a retention time of approximately 4 min with a detection level of 0.4 µg/mL.

Drug elution tests were performed using small blocks (1.0 cm×1.0 cm×1.0 cm) of polyethylene (n=6) and PE-BP (2% w/w of bisphosphonate, n=6) compression molded using a custom mold as previously described. Each polyethylene specimen was molded using 950±0.5 mg GUR® 4150 UHMWPE. Each PE-BP specimen was molded using the same amount of polyethylene (950±0.5 mg GUR® 4150 UHMWPE) with the addition of 019.4±0.2 mg alendronate sodium (ALN), a bisphosphonate (BP).

In vitro alendronate release study was performed in an environmental chamber maintained at 35°±2° C.; for the duration of the experiment, the specimens undergo shaking using a VWR mini shaker at 300 rpm. A 1 cm$^3$ block of polyethylene or PE-BP is placed into 10 mL of HPLC-grade water. Measurements were found using the HPLC methodology described above. HPLC measurements were repeated in triplicate.

Aliquots of 1 ml were taken over the course of 28 days (time points in hours): 1, 2, 4, 8, 12, 24, 48 (2 days), 72 (3 days), 120 (5 days), 168 (7 days), 336 (14 days), 404 (21 days), 572 (28 days). At the end of 28 days, the percent of drug eluted was calculated as determined by HPLC. The latter time points will show whether or not BP is migrating towards the surface of the PE-BP or remaining locked within the bulk region if no additional drug is released at later time points. Samples (n=6; triplicate) were analyzed using high pressure liquid chromatography (HPLC, Waters, Milford, Mass.) anion exchange using in-line complexation. A 6 mM nitric acid (Fluka)+1.5 mM copper II nitrate (Alfa Aesar) mobile phase were used at a flow rate of 0.85 mL/min using a Waters IC-Pak Anion HR column as previously described.

Blocks of UHMWPE composite were prepared using 2% (by weight) alendronate (Tecoland, Edison, N.J.) (PE-ALN) blended with UHMWPE powder (GUR® 4150 Ticona). All polyethylene specimens (PE and PE-ALN) were compression molded using a Carver press as described above. Polyethylene and PE-ALN pins of 9.5 mm shaft and 3 mm pin tip diameters were machined for pin-on-disk (POD) (Ortho-POD-AMTI, Watertown, Mass.) wear tests from two 12.7 mm thick blocks. Test parameters included: 40 km distance, 19 mm diameter circular pattern, 6 MPa contact tip pressure, diamond-coated CoCrMo counterpart. Tests were performed in 50% calf bovine serum with 0.2% sodium azide, Three pins of each material as well as 2 soak controls were used in individual trials with a total of 6 pins of each material experimentally tested. Each tribosystem was lubricated with 25 mL of 50% bovine serum diluted with deionized water; lubrication levels were monitored during the trial and deionized water was added as necessary to maintain appropriate serum levels. Soak controls were used as previously described. Six diamond-coated CoCrMo specimens (Ra=22.4±1.8 nm) mounted in custom fixtures were used as the countersurface. A 40-km were test was used (circle-shaped wear pattern 19 mm Ø wear pattern; 1 Hz), which is within ASTM standard F732 for pin-on-disk testing. Applied pin tip pressure was 6 MPa. Every 10 km, all specimens (experimental and soak controls) were cleaned (ASTM F1715 method). Additionally, the bovine serum was collected and frozen from each of the tribosystem for later HPLC analysis. Pins were imaged using non-contact surface profilometery (NT-2000 Non-Contacting Surface Profilometer; Wyko, Tucson, Ariz.).

Each of the specimens were dried in a vacuum oven maintained at 37° C. for a minimum of 30 minutes and then weighed (Mettler Toledo, d=0.01 mg). Once gravitational weights and imaging was complete, the OrthoPod was reassembled with application of new bovine serum. A two-tailed t-test ($\alpha$=0.05) was used to analyze the results for significance.

Bovine serum samples that were collected at the end of each 10 km segment were later thawed at room temperature for 4 hours. Bovine serum from six stations containing PE-ALN pins were used for this experiment with bovine serum thawed for each 10 km segment (24 total samples). In order to remove the proteins from the bovine serum so that it could be analyzed using HPLC, Microsep 3 k filters (Pall Life Sciences) were used. Samples were placed in the Microsep filters and then centrifuged at 3000 g for 180 min (in two 90 minute increments) using an Eppendorf Centrifuge 5702R. Then 1 mL of the resultant filtrate was removed using a syringe and filtered through a 0.45 µm polypropylene syringe filters (National Scientific) prior to injection in an HPLC vial (Waters). Samples were then analyzed as described above.

Results

Figure 5:
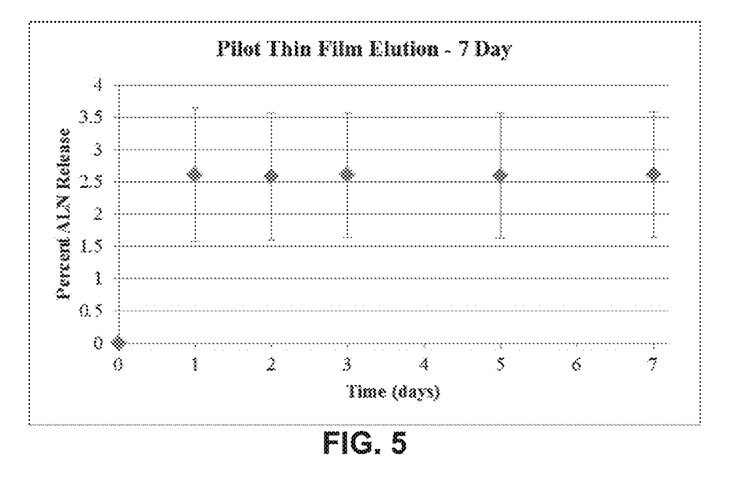
FIG. 5 illustrates the 7-day drug elution results from thin films formed of UHMWPE composites as described herein.

The 7-day drug elution tests showed ALN being eluted from the PE-BP thin films predominantly between day 0 and day 1 (FIG. 5). After Day 1, the graph remained flat indicating that there was negligible continued release from the 15 µm thick thin film samples. Control (PE) thin films showed no measurable peak at the ALN peak time (data not shown).

Figure 6A:
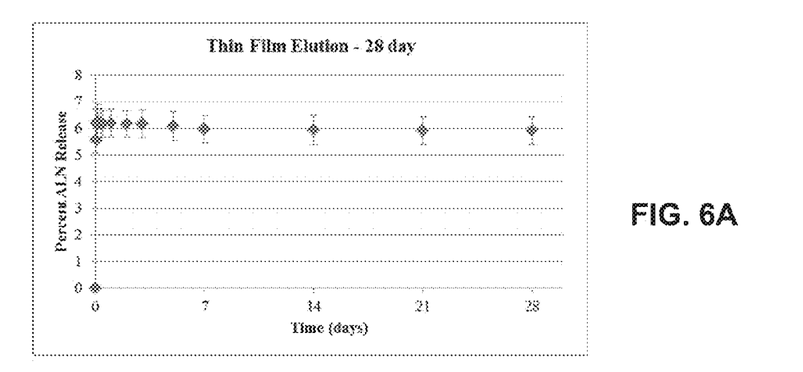
Figure 6B:
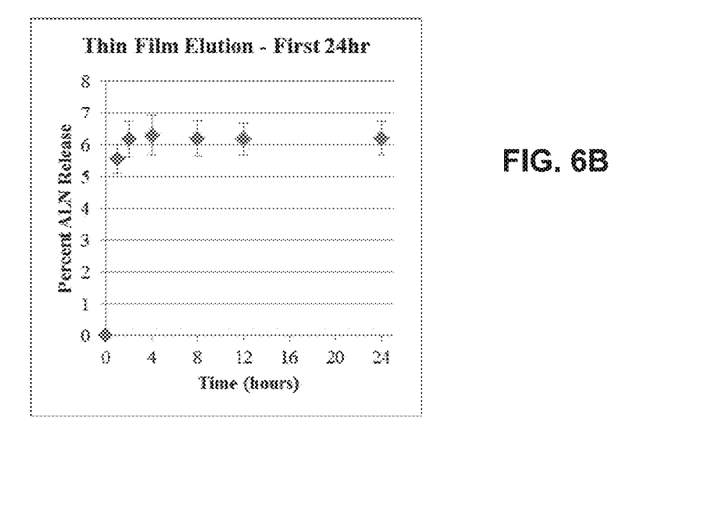

Longer studies (28-days) confirmed that most of the ALN that would elute is eluted within the first 24 hours. The 28-day thin film elution studies showed that the predominant portion of ALN eluting was within the first 4 hours and after 4 hours little to no ALN was eluting from these 15 µm thick thin films (FIGS. 6A and 6B). Total release was approximately 6% release from PE-BP thin films (60.5±2.2 µg).

Figure 7A:
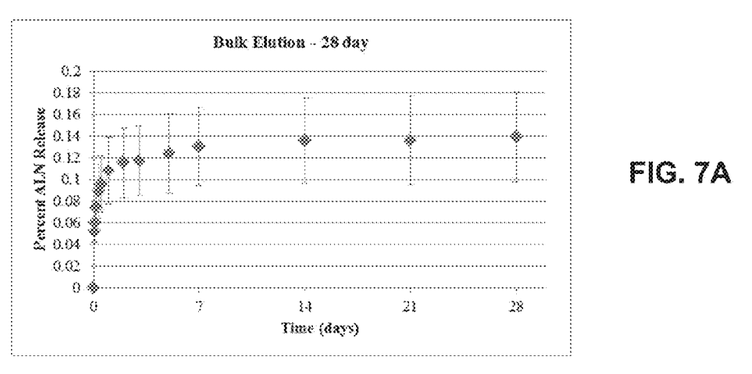
Figure 7B:
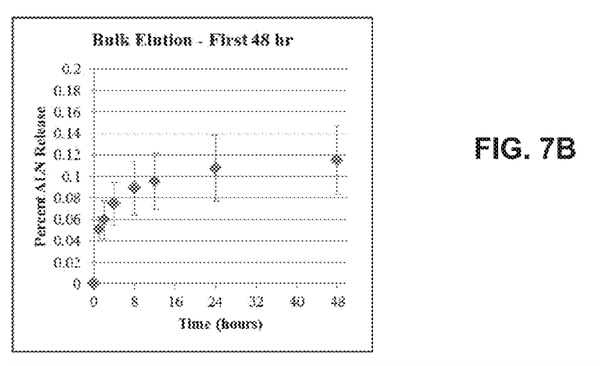
Figure 8:
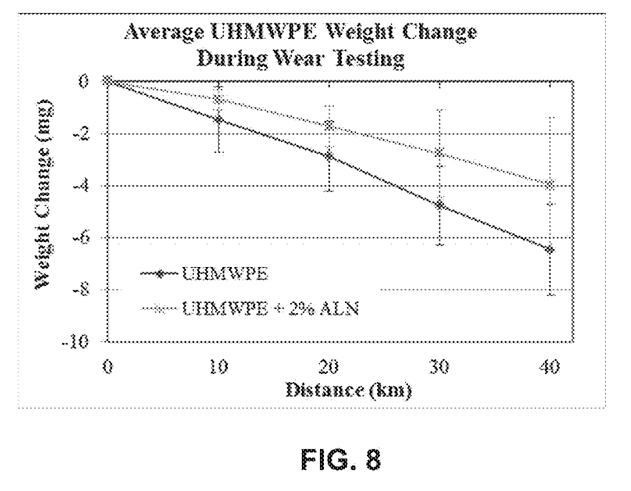
FIG. 8 compares the gravitational weight loss over 40 km wear test trial for UHMWPE composite pins and control UHMWPE pins.

Elution from the bulk samples showed similar results (FIG. 7A) with the majority of ALN being eluted within the first 24-hour time period (FIG. 8B). After day 14, little to no ALN continued to be released from the PE-ALN blocks. After 28 days, approximately 0.14±0.04% of the ALN had eluted from the bulk specimens (82.0±33.4 µg ALN). Again, no ALN peaks were evident in the control samples Results of the gravitational weight loss over the 40 km time period showed non-significant differences (p=0.26) for the PE-ALN and control pins. Data for each segment of the 40 km wear test is shown in FIG. 8.

Regardless of whether the sample was cut from the shallowest depth (0-15 um) or the deepest (106-120 um), there was 5-7% ALN release. Further, there was not a clear gradient of release where the higher release came from the exterior or the interior indicating that it is small inconsistencies of the mixing of the ALN within the material that is attributing to the variation. It should be noted however that these are in fact small differences and there was ALN present and being released at all depths showing that the drug did not accumulate at the bottom or top surface during molding. This is important as it allows for a continuous pool of ALN present within the PE-ALN components of a total joint replacement allowing extended release of the drug over an extended period of time.

From the results, it was evident that the ALN exhibited little migration as the bulk elution reached its maximum release over the 28 days by day 14 and then was constant afterward. This gives credit to the concept that the ALN will remain in the polyethylene once it is placed in vivo. Using the known surface area, volume, and density of each cube the depth of release can be calculated each block's respective drug elution at day 14, the calculated drug elution only occurs from the outer 0.05±0.01 micron of the blocks.

These results are in strong contrast to previous studies where BPs were encapsulated into Poly(D,L-lactide-co-glycolide-D-glucose) microspheres (abbreviated PLG-GLU), this UHMWPE appears to have a high enough hydrophobicity as well as a tight enough matrix that the 100% release within the first 24 hours seen with those microspheres has not been shown with the current material. The highly hydrophobic UHMWPE, even though it is known to absorb some liquid in aqueous environments, appears to maintain the ALN within its matrix even though ALN is highly hydrophilic.

Example 3

A total knee simulator experiment was conducted as a more rigorous wear test with generic right tibial plateau and femoral component. This design was selected to use already existent custom compression mold for the tibial insert allowing for compression molded components instead of machined.

Tibial components were molded using solely GUR® 4150 UHMWPE (Ticona) or GUR® 4150 UHMWPE with 2% alendronate sodium (ALN), a bisphosphonate (BP). Each polyethylene and PE-ALN specimen was molded using the same methodology previously described in Example 1.

A 4-station Stanmore/Instron Knee Simulator was used with two stations containing polyethylene and PE-ALN for a 2-million cycle experiment. The molded components were machined to lock within the tibial plateau. The bearing surfaces of these components were compression molded; however, to have proper use of the locking mechanism, grooves had to be machined into the anterior and posterior non-weight bearing surfaces of the components. Lubricant used was 50% defined calf bovine serum (Hyclone, Logan, Utah) diluted with deionized water+0.2% w/v sodium azide (NaN3, Sigma) as an anti-microbial agent per station. Approximately 0.5 L of the lubricant was cycled through each station throughout each segment of the trial. Each station had its own lubricant reservoir to minimize potential contamination. Lubricant containers were maintained at the base of the knee simulator with a sensor at the tibial cup to ensure that the stations always had lubricant. Additionally, the simulator was set to 'automatic pumping mode' so that lubricant was circulated every 10 minutes for the duration of the experiment. Due to evaporation, lubricant levels were checked and topped off twice a day to ensure that a 50% concentration of bovine serum was maintained.

Two of each of the samples (PE 1, PE 2, PE-ALN 1, PE-ALN 2) were wear tested. For 0 to 1 million cycles, the samples were removed and cleaned at every 250,000 cycles to assess early failure. For 1-2 million cycles, segments of 500,000 cycles were used. The testing environment was maintained at 35±2° C. to mimic physiological conditions. To supply and track the actual waveforms, an external computer interface was used (General Robotics Ltd., Milton Keynes, England) to ensure that the input waveforms were performing adequately. ISO standard 14243 for force controlled-simulators was used as a guideline for this experiment to determining appropriate waveform inputs with cycles occurring at 1 Hz. Waveforms inputs were determined through an iterative process prior to the start of the experiment; they were considered acceptable if the average deviation over the gait cycle was less than 10% of the ISO 14243 standard. Deviation from the ISO standard was monitored throughout the experiment.

The duration for the study was two million cycles, which represents approximately one year of use in patients. This experiment was aimed at elucidating whether PE-ALN does in fact wear at a similar rate to UHMWPE using a more rigorous test. Every 250,000 cycles (0-1M) or 500,000 million cycles (1-2M), the simulator was stopped to weigh the tibial inserts following cleaning and drying. All the test specimens were cycled between stations every 250,000 or 500,000 million cycles depending on which segment of the test was occurring. This was done to minimize the effects of inter-station variability on resulting wear rates as there were slight differences in the roughnesses of each of the four femurs.

Kinematic and kinetic data were recorded by logging files from the simulator approximately every 12 hours. Each file included 15 seconds of data measured at 50 Hz. Logged files were assessed daily to ensure that simulator operation was maintained within 10% of the ISO standard. Files included information such as flexion angle, axial load, anterior/posterior displacement, internal/external tibial rotation, anterior/posterior implant shear reaction force, and internal/external implant reaction torque.

Two specimens of each material (PE 3, PE 4, PA-3 and PA-4; PA including the ALN additive) were maintained as non-loaded soak controls in 50% bovine serum with 0.2% sodium azide within a 35°±2° C. environmental chamber to allow for calculation of fluid absorbed into the specimens. The tibial inserts (both experimental and soak) were cleaned using ASTM F1715 method at the end of each interval (¼ or ½M cycles). After cleaning, the tibial inserts were allowed to dry for 24 hours in a desiccator under vacuum prior to weighing (Mettler Toledo, d=0.01 mg). Tibial components, cups holding the components and the tubing in the knee simulator were cleaned with a bleach and detergent mixture at each time point.

Non-contact profilometery and stereomicroscopy were conducted at 0 and 2 million cycles to analyze the surface for microscopic changes in wear that may not be apparent via the gravimetric weights. Non-contact profilometery (NT-2000 Non-Contacting Surface Profilometer; Wyko, Tucson, Ariz.) was performed on 8 points per insert (4 points/condyle) prior to and after the experiment. The gross images of the tibial inserts were recorded using stereomicroscopy (Model K400P, Motic Inc, Xiamen, China) at 6× & 12× magnification to view the center of medial and lateral bearing surfaces at the beginning and end of the study (0 and 2M cycles). Stereomicroscope used attachments for image acquisition including a fluorescent ring lamp illuminator and a color digital camera (Model Inifinity 2-1C, Lumenera Corp., Ottawa, Ontario, Canada) with 1392×1040 pixel resolution.

The femurs were analyzed using non-contact profilometry (6 points per condyle (12 points/femur)) and stereomicroscopy (12×, 6 points/femur) before and after the experiment. Further, two tibial plateaus were imaged using a Hitachi S-3400N SEM after experimentation had finished to compare the surfaces within the wear condylar wear path. Variable pressure (30 Pa) SEM at 100× and 250× was used to investigate the primary modes of wear. It was expected that these would be polishing and burnishing, however, as this is a composite material other modes may be seen such as abrasion if the drug is harder than the polyethylene and scratches its surface. Additionally, Energy-dispersive X-ray spectroscopy (abbreviated EDX or EDS) was used to analyze the surface to evaluate whether there was ALN on the surface of the tibial inserts.

Calculation of wear was soak control-corrected using the gravimetric weights from the 4 specimens in the environmental chamber. Two-tailed t-tests ($\alpha=0.05$) were used to analyze the results for significance.

Results

The ISO standard for walking was followed during the trial with the results of the maintenance of the waveform within 10% of the ISO standards. Flexion, axial, and internal/external torque were maintained within the 0-5% error range throughout the experiment while A/P actuation force was maintained within the 5-7.5% error range.

Using non-contact profilometery, it was found that the 4 femurs had an average roughness of 43.5±23.4 nm at the beginning of the TKR experiment.

Stereomicroscopy was also completed of the femurs (12×) prior to starting the test to have a better visualization of the differences in roughness among the femoral components. It was clearly seen that the femurs had abrasion along the wear track.

The roughness of the polyethylene and PE-ALN components were found to decrease by 31.6% and 56.4% respectively (Table 4, below). There was not a significant difference in the Ra (p=0.51) or Rq (0.57) values at 0M between the two materials. At 2 million cycles, PE-ALN was significantly rougher than the polyethylene only, both for Ra (Ra, p=0.002) and Rq (0.01).

TABLE 4

| | Ra | | Rq | |
|---|---|---|---|---|
| | PE | PE-ALN | PE | PE-ALN |
| 0M | 156.8 ± 53.7 | 276.4 ± 127.5 | 221.3 ± 66.1 | 388.6 ± 176.3 |
| 2M | 107.3 ± 46.6* | 120.5 ± 30.6* | 138.8 ± 56.9‡ | 154.3 ± 41.0‡ |

*p = 0.002
‡p = 0.01

Stereomicroscopy was also completed before and after the experiment. Images from the beginning of the experiment showed uniform compression molded surfaces for both materials with a few scratches from the molding process. Images at 2M cycles exhibited the expected wear track on both condyles. Images from the center of the wear track show burnishing and scratching. It was evident at the anterior and posterior of the tibial insert the delineation between the wear path and the unworn compression molded surfaces. Additionally, bisphosphonate was apparent in the surfaces of the PE-ALN samples at both timepoints.

The SEM images showed non-worn specimens at 0M. These specimens showed residual Teflon® in the outer surface of the implant as evidenced by the white spots on the SEM images. This was confirmed using EDX. The only peaks shown in the EDX spectra were carbon (C) and fluorine (F). UHMWPE is comprised of carbon and hydrogen while Teflon® is comprised of carbon and fluorine. No ALN (specifically the phosphorus) was found using EDX. The primary modes of wear that were observed in the images were scratching and burnishing.

Figure 9:
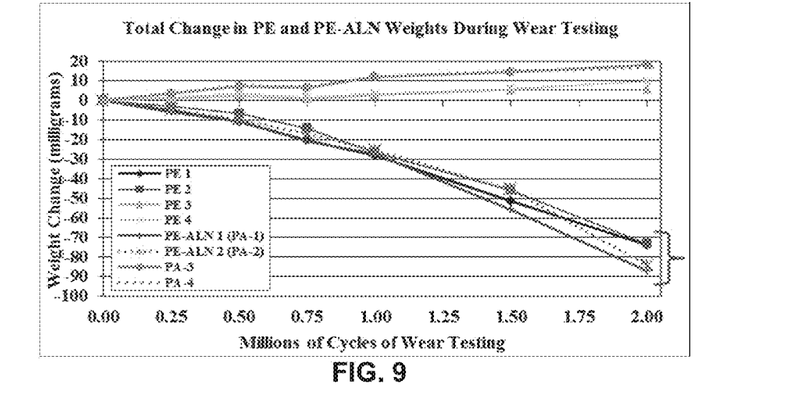
FIG. 9 summarizes the total change in weight of several UHMWPE controls and UHMWPE composites as described herein over 2M cycles in a total knee joint simulator trial.
Figure 10:
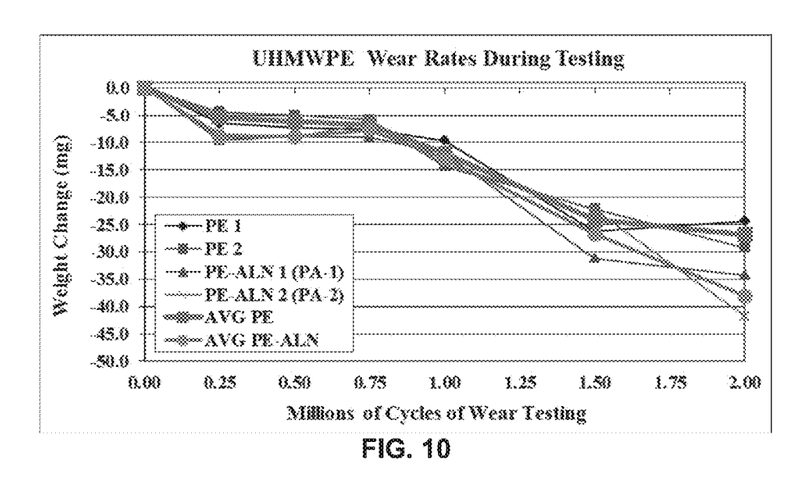
FIG. 10 summarizes the soak control corrected total change in weight of several UHMWPE controls and UHMWPE composites as described herein over 2M cycles for the total knee joint simulator experiment.
Figure 11:
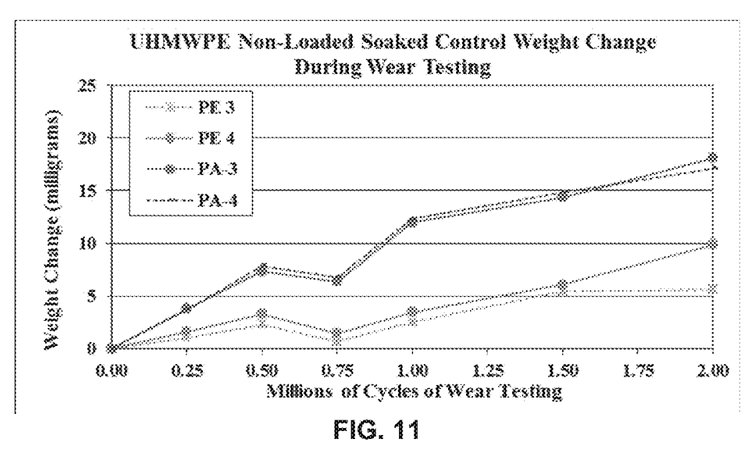
FIG. 11 is an expanded view of non-loaded soak control replacement knee joint specimens over 2 million cycles p=0.14.
Figure 12:
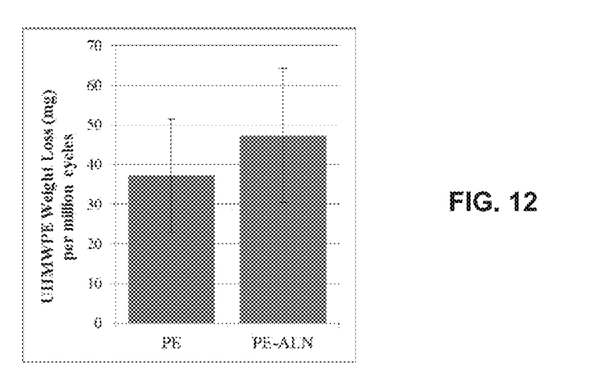
FIG. 12 compares the average per-million weight loss of replacement knee joints incorporating a control UHMWPE and an UHMWPE composite as described herein over 2M cycle trial.

All wear tested specimens showed steady raw weight loss over the 2M cycle trial (FIG. 9, FIG. 10). Further, the soak control specimens continued to gain weight over the course of the trial (FIG. 9, FIG. 11). As can be seen, over the 2 million cycles the tibial components showed similar gravitational loss (FIG. 10). The lines diverged more at 2M. The average weight loss per million cycles was not statistically different between the two materials (p=0.14) with 37.2±14.2 mg for polyethylene and 47.3±16.9 mg for PE-ALN (FIG. 12).

While certain representative embodiments and details have been shown for the purpose of illustrating the subject invention, it will be apparent to those skilled in this art that various changes and modifications may be made therein without departing from the scope of the subject invention.

What is claimed is:

1. A joint replacement comprising a component, the component comprising an ultra-high molecular weight polyethylene composite, the ultra-high molecular weight polyethylene composite including a biologically active agent blended with the ultra-high molecular weight polyethylene such that the biologically active agent is distributed homogenously or heterogeneously throughout the component.

2. The joint replacement according to claim 1, wherein the biologically active agent is an anti-osteolytic biologically active and/or an osteogenic agent.

3. The joint replacement according to claim 2, wherein the biologically active agent is a bisphosphonate.

4. The joint replacement according to claim 3, wherein the bisphosphonate is selected from the group consisting of etidronate, clordronate, tiludronate, pamidronate, neridronate, olpadronate, alendronate, ibandronate, risedronate, zoledronate, and combinations thereof.

5. The joint replacement according to claim 1, wherein the biologically active agent is blended with the ultra-high molecular weight polyethylene such that the composite includes the biologically active agent in an amount of up to about 5% by weight of the composite.

6. The joint replacement according to claim 1, further comprising a second component comprising a cobalt/chromium/molybdenum alloy or a ceramic alloy.

7. The joint replacement according to claim 1, the composite further comprising an additive blended with the ultra-high molecular weight polyethylene and the biologically active agent.

8. The joint replacement according to claim 7, wherein the additive is a fibrous additive.

9. The joint replacement according to claim 8, wherein the fibrous additive comprises ultra-high molecular weight fibers.

10. The joint replacement according to claim 1, wherein the biologically active agent is homogeneous throughout the ultra-high molecular weight composite.

11. The joint replacement according to claim 1, wherein the biologically active agent is heterogeneous throughout the ultra-high molecular weight composite.

12. The joint replacement according to claim 1, the component defining a wear surface, the component including a first area and a second area, the first area being generally parallel to the wear surface and at a depth to the wear surface, wherein the concentration of the biologically active agent is higher within the first area as compared to the concentration of the biologically active agent within the second area.

13. The joint replacement according to claim 1, wherein the joint replacement is a total joint replacement.

14. The joint replacement according to claim 1, wherein the joint replacement is a total knee replacement or a total hip replacement.

15. A method for forming the joint replacement of claim 1, the method comprising:
   blending the ultra-high molecular weight polyethylene with the biologically active agent to form the composite; and
   shaping the composite to form the component of the joint replacement, wherein the component comprises a wear surface.

16. The method according to claim 15, wherein the step of blending the ultra-high molecular weight polyethylene with the biologically active agent comprises melt processing the ultra-high molecular weight polyethylene.

17. The method according to claim 15, wherein the joint replacement is a total knee replacement or a total knee replacement.

18. The method according to claim 15, wherein the biologically active agent is an anti-osteolytic and/or osteogenic agent.

19. The method according to claim 18, wherein the biologically active agent is a bisphosphonate.

* * * * *

UNITED STATES PATENT AND TRADEMARK OFFICE
CERTIFICATE OF CORRECTION

| | | |
|---|---|---|
| PATENT NO. | : 8,858,979 B1 | Page 1 of 1 |
| APPLICATION NO. | : 13/360020 | |
| DATED | : October 14, 2014 | |
| INVENTOR(S) | : John D. DesJardins et al. | |

It is certified that error appears in the above-identified patent and that said Letters Patent is hereby corrected as shown below:

In the Claims

Column 18, lines 54 - 55 "...total knee replacement or a total knee replacement" should read -- total knee replacement or total hip replacement. --

Signed and Sealed this
Fifteenth Day of September, 2015

Michelle K. Lee
*Director of the United States Patent and Trademark Office*